US010201239B2

United States Patent
Ahroon

(10) Patent No.: US 10,201,239 B2
(45) Date of Patent: Feb. 12, 2019

(54) HEADPHONE CASE HAVING FIXED OR INFLATABLE CUSHION

(71) Applicant: Erik Ahroon, Newport Beach, CA (US)

(72) Inventor: Erik Ahroon, Newport Beach, CA (US)

(73) Assignee: MOUSIKI, INC., Corona Del Mar, CA (US)

( * ) Notice: Subject to any disclaimer, the term of this patent is extended or adjusted under 35 U.S.C. 154(b) by 939 days.

(21) Appl. No.: 14/590,830

(22) Filed: Jan. 6, 2015

(65) Prior Publication Data

US 2015/0297003 A1   Oct. 22, 2015
US 2018/0098647 A9   Apr. 12, 2018

Related U.S. Application Data

(60) Provisional application No. 61/924,670, filed on Jan. 7, 2014.

(51) Int. Cl.
| | |
|---|---|
| *A47G 9/00* | (2006.01) |
| *A47G 9/10* | (2006.01) |
| *A45C 11/00* | (2006.01) |
| *A61B 6/00* | (2006.01) |
| *G06T 7/33* | (2017.01) |
| *G06T 7/11* | (2017.01) |

(52) U.S. Cl.
CPC ............ *A47G 9/1045* (2013.01); *A45C 11/00* (2013.01); *A47G 9/1027* (2013.01); *A47G 9/1081* (2013.01); *A61B 6/5235* (2013.01); *G06T 7/11* (2017.01); *G06T 7/33* (2017.01); *A45C 2011/001* (2013.01); *A61B 6/505* (2013.01); *G06T 2207/10081* (2013.01); *G06T 2207/10088* (2013.01); *G06T 2207/10104* (2013.01); *G06T 2207/30008* (2013.01)

(58) Field of Classification Search
CPC ....... A47C 7/383; B60N 2/4876; A45C 11/00; A45C 2011/001; A47G 9/1045; A47G 9/1027; A47G 9/1081
USPC ....................................... 206/320, 38; 5/639
See application file for complete search history.

(56) References Cited

U.S. PATENT DOCUMENTS

| | | | | |
|---|---|---|---|---|
| 5,257,420 A | * | 11/1993 | Byrne, Jr. | ............... A61F 11/06 |
| | | | | 2/209 |
| 5,313,678 A | * | 5/1994 | Redewill | .............. A47C 21/003 |
| | | | | 297/393 |

(Continued)

*Primary Examiner* — Steven A. Reynolds

(57) ABSTRACT

A headphone case is provided that serves as both a case for storing headphones and other objects, and a cushion to be worn around the neck. The case has either a fixed cushion located on different parts of the case, or a material that can be inflated, where the material has an outside layer comprising a cushion material. The case has two halves, a top half and lower half, which are held together by one or more hinges or other means. The headphone case can have a control unit for electronically inflating the material on the case, and for controlling units inside the case for controlling an amount and intensity of heat and vibration. Software can be uploaded to the control unit via a USB port or a Bluetooth antenna for controlling the different functions of the case. An application running on a phone, tablet or computer may control the functions of the various units inside the case.

17 Claims, 4 Drawing Sheets

(56) References Cited

U.S. PATENT DOCUMENTS

| | | | | |
|---|---|---|---|---|
| 5,344,437 | A * | 9/1994 | Pistay | A61F 7/10 5/639 |
| 8,887,333 | B2 * | 11/2014 | Cohen | A47C 7/383 5/636 |
| 9,003,582 | B2 * | 4/2015 | Armbruster | A61M 21/02 381/333 |
| 2006/0001307 | A1 * | 1/2006 | Embach | B60N 2/4876 297/391 |
| 2007/0256946 | A1 * | 11/2007 | Godshaw | B65D 25/10 206/320 |
| 2014/0007351 | A1 * | 1/2014 | Cohen | A47G 9/10 5/639 |
| 2014/0310877 | A1 * | 10/2014 | Sternlight | A47G 9/10 5/639 |
| 2016/0022045 | A1 * | 1/2016 | Lee | B60N 2/4876 5/639 |

* cited by examiner

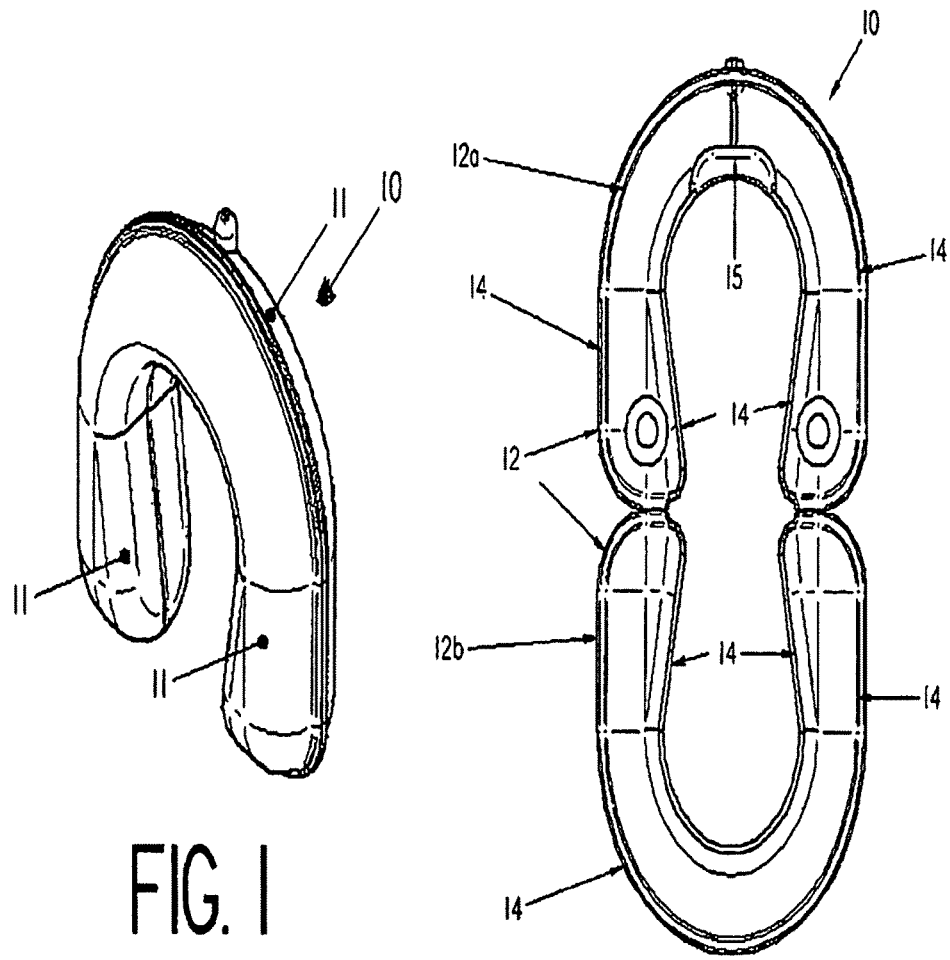

HEADPHONE CASE HAVING FIXED OR INFLATABLE CUSHION

CROSS REFERENCE TO RELATED APPLICATIONS

This application is a non-provisional continuation of U.S. Provisional Application 61/924,670, filed Jan. 7, 2014, which is incorporated by reference in its entirety.

FIELD OF THE INVENTION

The present invention relates generally to the field of headphone cases, and more specifically to a headphone case that has a fixed or inflatable cushion to provide comfort and support for a neck and an area for storing headphones.

BACKGROUND OF THE INVENTION

Traveling can be absolutely exhausting especially in an airplane. The everyday hassle and stress associated with logistics can be overwhelming for weekly or daily travel by air. Some travelers pack as light as possible to avoid checking in bags at an airport and remain nimble with their evolving schedules to choose only necessary items. Two items carried by some travelers is a pair of headphones and a head cushion which may be inflatable. Both provide some level of comfort and disassociation with plane travel.

In a plane, a headphone case is typically stored below the seat in front of the traveler or in the small pocket in the seat in front of the traveler. After the headphones are removed from the case, the case is not utilized until travel is over when the headphones are then placed back into the case.

Therefore, what is needed is a headphone case that can double as a case for storing headphones and acts as a cushion for providing comfort and support for a neck.

SUMMARY OF THE INVENTION

Accordingly, the present invention encompasses a case having a fixed or inflatable cushion. The headphone case is preferably a U-shape or a donut-shaped design to conform to the neck and head of a person. When the case is closed, the body or shell forms an area that can be used for storing headphones or other objects, such as eyeglasses, a toothbrush, or comb for example.

An object of the present invention is to provide a case having the dual functionality of a providing headrest that fits around the neck, and a case for storing headphones therein.

Another object of the present invention is to include a vibration mechanism in the case for massaging the neck.

Yet another object of the present invention is to provide a heater in the case for comfort and relaxation.

Another object of the present invention is to lighten the load of a traveler, providing dual functionality of a headphone case for the traveler, and adding value to a component which would otherwise be stored (in a compartment, bin, seat, etc.) during travel or lost.

The present invention is a case comprising a "U"-shaped body, having a top half and a lower half, and material attached to one or more portions of the body, the material having a cushion.

The present invention also is a case comprising a body, having a top half and a bottom half, where the top half and the bottom half form a space when joined together in a closed position for fitting around a neck of a person, and material attached to one or more portions of the body.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings. It is to be understood that both the foregoing general description and the following detailed description are exemplary and explanatory and are intended to provide further explanation of the invention as claimed and not to limit it.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 1 illustrates a front perspective view of a case according to an embodiment of the present invention.

FIG. 2 illustrates an open position of a case according to an embodiment of the present invention.

DETAILED DESCRIPTION OF THE PREFERRED EMBODIMENT

Figure 3:
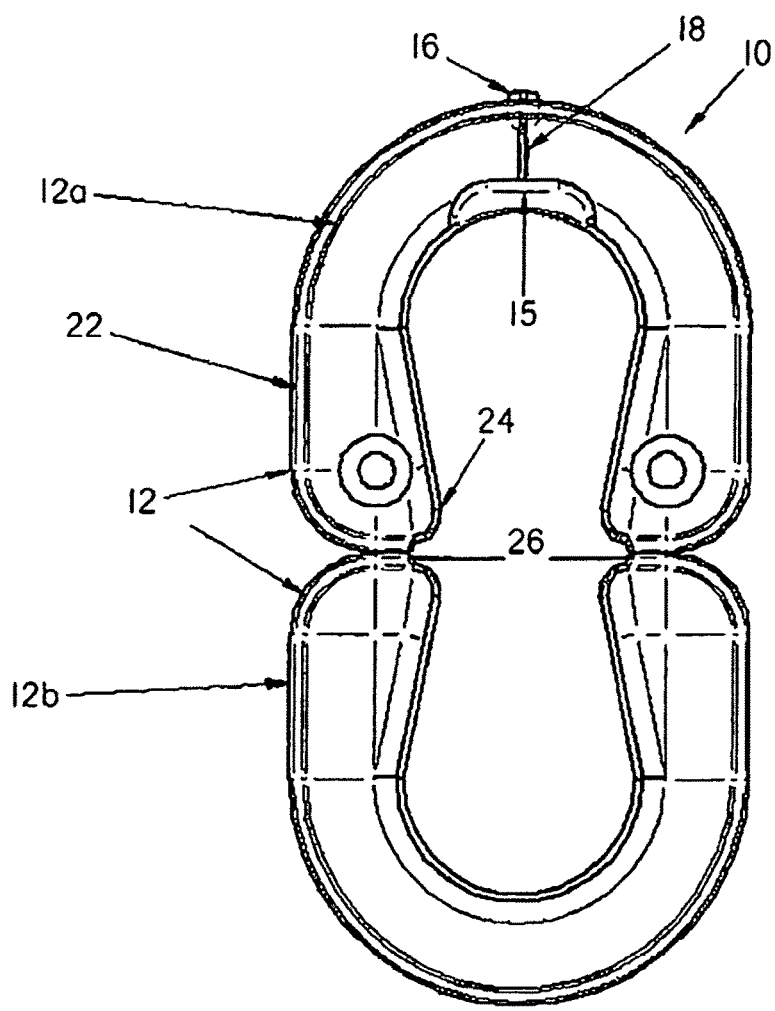
FIG. 3 illustrates an open position of a case according to an embodiment of the present invention.
Figure 4:
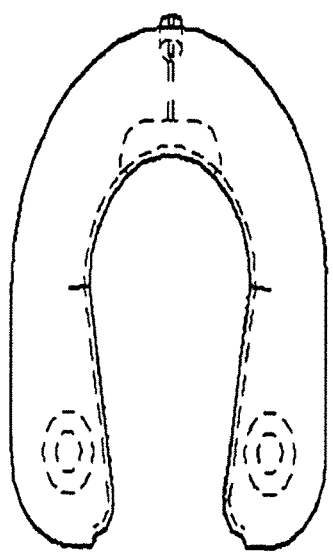
FIG. 4 illustrates a side view of a case according to an embodiment of the present invention.
Figure 5:
FIG. 5 illustrates a back perspective view of a case according to an embodiment of the present invention.
Figure 6:
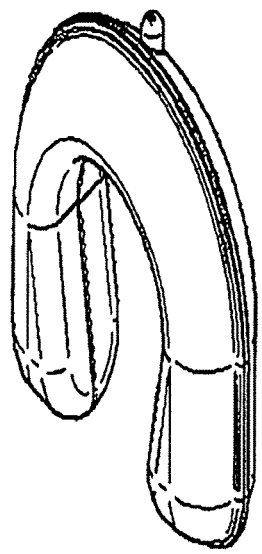
FIG. 6 illustrates a left-side front perspective view of a case according to an embodiment of the present invention.

FIG. 1 illustrates a front perspective view of a case 10 having a fixed cushion 11 according to a preferred embodiment of the present invention. In this embodiment, case 10 has a fixed cushion 11 attached to certain portions of the outside of case 10. As illustrated in FIG. 1, case 10 is shaped in a "U" and is illustrated to be in the closed position. In other embodiments, other shapes of case 10 could be used as well, including for example, a donut or "0" shape. Case 10 serves a dual purpose: to provide a headrest for around a neck of a person, and a case 10 for storing headphones or other items. Case 10 could be worn around the neck to provide support and comfort during travel, especially during air travel.

FIG. 2 illustrates an open position of a case 10 having a fixed cushion 11 according to an embodiment of the present invention. In this embodiment, case 10 comprises an inner body 12 comprising a top half 12a and a bottom half 12b, and a layer of material 14 having a soft cushion on the outside of body 12. Body 12 can be molded or formed from plastic or any other suitable material. Body 12 has adequate physical dimensions so when case 10 is in a closed-position, headphones and other items or objects can be stored therein. Case 10 is in a closed position as shown in FIG. 1. The headphones that can be stored inside case 10 are those typically having a headband and earcups that fit onto or around the ear, including for example those headphones manufactured by Bose, Sony, JVC, Panasonic and Beats.

Cushion or material 14 can be any material commercially available to provide cushion and comfort to a neck and a head of a person, for example, foam, memory foam or Temper-Pedic® materials. Although material 14 preferably is attached to and covers both top half 12a and bottom half 12b of case 10, in other embodiments, material 14 can be on select portions of body 12. For example, material 14 may be attached to the top half 12a and a portion of the bottom half 12b that rests on the neck and shoulders.

Case 10 can be closed where top half 12a of case 10 has a lip or edge that fits over bottom half 12b. In the closed position as illustrated in FIG. 1, case 10 stays closed via zippers (not shown), snap hooks, belts, sliding claps, or any other way for holding top half 12a and bottom half 12b in a closed position.

As shown in FIG. 2, a compartment 15 is built into the top half 12a of body 12. Compartment 15 could store a commercially available power-operated vibration unit, a commercially available heater, or a combination of those units. These vibration and heater units can be battery-operated or connected to a power outlet (including those on an airplane) via an electrical cord. A plug or an outlet would be provided somewhere on the outside of body 12 or case 10. Batteries for powering the heater or vibration unit could be stored in compartment 15 or another place inside body 12. The functions for controlling the vibration and heater units, including the intensity of the vibration and the amount of heat, are controlled remotely by a remote control unit, or via a Bluetooth connection to a smartphone, tablet or other device (which is running an application for such control), or one or more dials or buttons located inside or outside of case 10 (not shown).

FIG. 3 illustrates an open, top perspective view of a case 10 according to an embodiment of the present invention. In this embodiment, the cushion or material 14 located on the outside of case 10 or stored inside case 10 is inflatable. As shown in FIG. 2, case 10 comprises body 12 (including a top half 12a and a bottom half 12b), nozzle 16, connection tube 18, compartment 15, outside zipper 22, inside zipper 24 and hinges 26. Body 12 comprises a top half 12a and a bottom half 12b. In alternative embodiments, body 12 may be single piece or shell with compartments or openings for accessing the headphones or other items stored therein. Body 12 can be a shell as illustrated in FIG. 2 that provides an area for storing headphones when case 10 is closed (i.e., when top half 12a and bottom half 12b are joined together). Although body 12 is preferably a firm, durable shell material, in alternative embodiments, body 12 could have a flexible (and inflatable) composition, such as flexible plastic for example.

Body 12 comprises a "U"-shaped design, which is shown in FIG. 3 to be in the open position and in FIGS. 1 and 4-6 in the closed position. As previously mentioned, case 10 or body 12 could have other shapes and sizes than what is shown in FIG. 3. Top half 12a and bottom half 12b of body 12 are attached to and held together by hinges 26 as illustrated in FIG. 2. Hinges 26 can be plastic or any suitable material or composition (e.g., steel, tin, aluminum) for joining top half 12a and bottom half 12b together. Although hinges 26 attach to the end of the "U"-shaped case 10 as shown in FIG. 3, in alternative embodiments, one or more hinges 26 could be attached to other places on body 12. Case 10 may also have snap locks or other commercially available ways for closing and securing the two halves 12a, 12b together when case 10 is in a closed position. An outside zipper 22 and an inside zipper 24 are attached to body 12. Outside zipper 22 and inside zipper 24 are commercially available and would be used for opening and closing case 10.

On the side opposite to what is illustrated in FIG. 2, a commercially available inflatable material is attached to the outside of body 12. This inflatable material can be layered on the top layer with a commercially available, soft, cushiony material or velvety layer to provide extra level of comfort for the neck or head. The inflatable material can be located on the outside of top half 12a and bottom half 12b of case 10, on one of the halves 12a or 12b of case 10, or on a specific part or area of case 10, such as the outside portion of body 12 that would fit around the neck. The inflatable material forms a pocket on all or some part of case 10 by how the inflatable material is attached to body 12. Tubes (not shown) may connect inflatable material which is separately located on body 12. The tubes would be located on the inside of body 12.

In alternative embodiments, case 10 may have one or more enclosures or pockets where the inflatable material would be stored. The enclosures or pockets would be unzipped or otherwise opened to release the inflatable material before it is inflated.

In the preferred embodiment, case 10 can be inflated by manually blowing air through nozzle 16 which then passes through the connection tube 18 into the inflatable material. As illustrated in FIG. 3, case 10 has a nozzle 16 located at the bottom of "U"-shaped body 12. In other embodiments, one or more nozzles 16 could be located at other positions on body 12. There also may be multiple nozzles 16, one on each half of the body. Nozzle 16 is commercially available and provides a way for air to inflate and deflate the inflatable material. Nozzle 16 can be fabricated or already incorporated into the inflatable material. Inflatable material can be deflated by opening nozzle 16 and letting the air release through nozzle 16. Nozzle 16 may have an end-cap that stops air flow when removed from nozzle 16, or some other commercially available design where compression of the nozzle 16 permits the entry or release of air.

Figure 7:
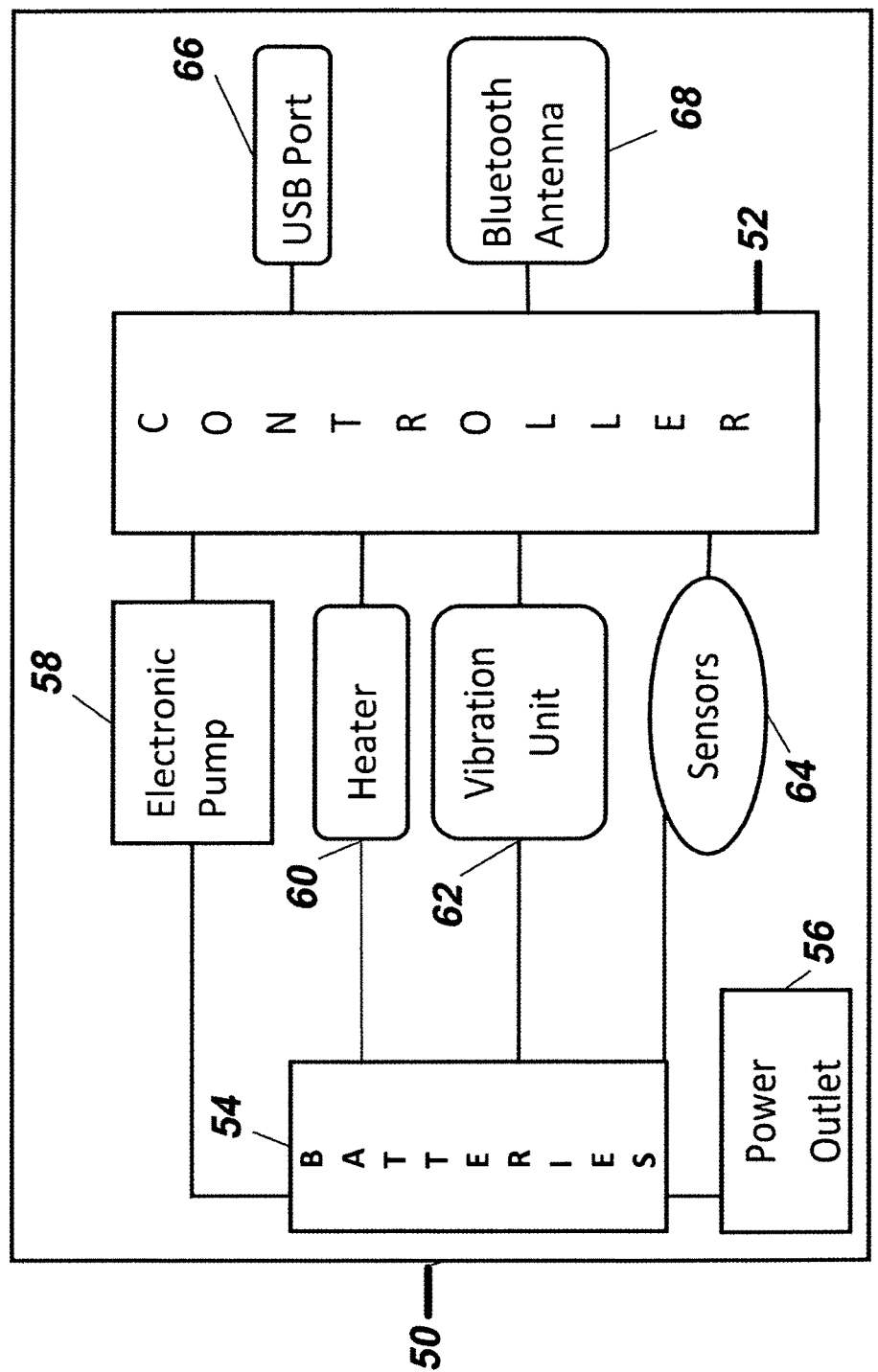
FIG. 7 shows a control unit according to an embodiment of the present invention.

FIG. 7 shows a control unit 50 for providing and controlling different functions and features of the headphone case 10 according to an embodiment of the present invention. Control unit 50 comprises a controller 52, batteries 54, power outlet 56, electronic pump 58, heater 60, vibration unit 62, sensors 64, USB port 66 and Bluetooth antenna 68. Control omits unit 50 can be designed using some of these parts and components rather than all of those shown in FIG. 7. Controller 52 is a commercially available microprocessor having built in memory for storing software (which can be downloaded via the USB port 66 or Bluetooth antenna 68). Although memory may be integrated into controller 52, in some embodiments, a memory unit could be incorporated in control unit 50. Batteries 54 are preferably commercially available rechargeable lithium batteries, but other commercially available batteries could be used as well. Power outlet 56 provides a way for plugging into a power source to recharge batteries 54 or to directly provide power to control unit 50.

A commercially available electronic pump 58 could be used to inflate and deflate the inflatable material. The electronic pump 58 could be powered via batteries 54 or may connect via power outlet 56 to a power source including but not limited to those outlets available on airplanes. Control unit 50 also includes a commercially available heater 60 for providing heat to the headphone case 10, and a commercially available vibration unit 62 for providing soothing vibration to a neck via the headphone case 10. The heater 60 may have heater coils or threads that extend from the heater 60 along the body 12 of case 10. Commercially available sensors 64 provide a way for detecting levels of stress and relaxation by measuring body temperature, pulse, or other physical conditions. Sensors 64 operate in conjunction with a variety of software programs stored in controller 52 to adjust levels of heat and vibration according to the program or until a particular biometric condition is reached.

A remote control unit (not shown) can provide a way to control the functions of control unit 50, including the electronic pump 58, heater 60 and vibration unit 62. The remote control unit would communicate with the control unit 50 through the Bluetooth antenna 68 or via a USB port 66. Controller 52 may be programmed with a series of programs whereby the heater 60 and vibration unit 62 could be sequenced on and off, or where the intensity and location of the heat and vibration would be dissipated around the headphone case 10 to target different neck or shoulder muscles.

In alternative embodiments, case 10 has a U-shaped design and a removable comfort liner. The comfort liner would be made of a comfortable material and would attach to some part of the body 12, such as the inner "U" segment of body 12, to provide a smooth comfortable surface for the neck and upper shoulders. When case 10 is in the closed position, the comfort liner can be attached to both the top half 12a and bottom half 12b, and attached to by several means (Velcro, buttons, zippers, etc.) to provide a comfortable surface on the user's neck and shoulders. When the liner is not being used, the liner could be stored inside case 10.

While the invention has been described in detail and with reference to specific embodiments thereof, it will be apparent to those skilled in the art that various changes and modifications can be made therein without departing from the spirit and scope thereof. Although the description above focused on a case providing a headrest and a headphone case, it should be apparent to one skilled in the art that the case of the present invention can be used for storing a variety of items other than headphones. Thus, it is intended that the present invention cover the modifications and variations of this invention provided they come within the scope of the appended claims and their equivalents.

What is claimed is:

1. A headphone case comprising:
   a "U"-shaped body, having a top half and a bottom half, wherein each of the top half and the bottom half have a U-shaped cross-section when the headphone case is in an open position and in a closed position, and wherein the top half and the bottom half form a space therebetween for storing headphones along the "U"-shaped body when joined together in a closed position;
   at least one hinge that couples two portions of the top half to two portions of the bottom half of the "U"-shaped body; and
   material attached to one or more portions of the body, wherein the material has a cushion.

2. The headphone case of claim 1, wherein the cushion is a foam material having an outside protective layer.

3. The headphone case of claim 1, wherein the body has physical dimensions to store the headphones when the body is in the closed position.

4. The headphone case of claim 1, wherein the material is inflatable.

5. The headphone case of claim 4, further comprising a nozzle attached to the inflatable material, wherein the nozzle is located at a bottom of the "U"-shaped body.

6. The headphone case of claim 1, further comprising a control unit which includes a controller and one or more batteries coupled to the controller.

7. The headphone case of claim 6, wherein the material is inflatable, and wherein the control unit includes an electronic pump coupled to the controller and the one or more batteries.

8. The headphone case of claim 6, wherein the control unit includes a heater coupled to the controller and the one or more batteries.

9. The headphone case of claim 6, wherein the control unit includes a vibration unit coupled to the controller and the one or more batteries.

10. The headphone case of claim 6, wherein the control unit includes at least one of a USB port and a Bluetooth antenna.

11. The headphone case of claim 6, wherein the control unit includes a power outlet that is coupled to the one or more batteries.

12. The headphone case of claim 1, further comprising a compartment located at a center of the top half of the "U"-shaped body.

13. A case comprising:
    a body, having a top half and a bottom half, wherein each of the top half and the bottom half have a U-shaped cross-section when the case is in an open position and in a closed position, and wherein the U-shaped cross-section allows for fitting around a neck of a person when the case is in the closed position, and wherein the top half and the bottom half form a space therebetween for storing an item when joined together in the closed position;
    at least one hinge that couples two portions of the top half to two portions of the bottom half of the "U"-shaped body; and
    material attached to one or more portions of the body.

14. The case of claim 13, wherein the material is a foam cushion or inflatable plastic.

15. The case of claim 13, further comprising:
    an outside zipper for joining outside portions of the top half and the bottom half; and
    an inside zipper for joining inside portions of the top half and the bottom half.

16. The case of claim 13, wherein the item is a headphone.

17. A case comprising:
    a body having a U-shape for fitting around a neck of a person, the body having a top half and a bottom half, wherein each of the top half and the bottom half have a U-shaped cross-section when the case is in an open position and in a closed position, and wherein the top half and the bottom half form an interior space therebetween for storing headphones along the U-shape when joined together in a closed position;
    at least one hinge that couples two portions of the top half to two portions of the bottom half of the "U"-shaped body; and
    material attached to one or more portions of the body.

* * * * *